US006574359B1

(12) United States Patent
Hance

(10) Patent No.: US 6,574,359 B1
(45) Date of Patent: Jun. 3, 2003

(54) METHOD AND APPARATUS FOR INSPECTING WAFER DEFECTS

(75) Inventor: Bryon K. Hance, Austin, TX (US)

(73) Assignee: Advanced Micro Devices, Inc., Sunnyvale, CA (US)

( * ) Notice: Subject to any disclaimer, the term of this patent is extended or adjusted under 35 U.S.C. 154(b) by 0 days.

(21) Appl. No.: 09/498,242

(22) Filed: Feb. 3, 2000

(51) Int. Cl.[7] .................................................. G06K 9/62

(52) U.S. Cl. .................... 382/149; 250/370.1; 356/622; 356/237.4

(58) Field of Search ............................... 382/144, 145, 382/147, 149, 154; 250/265, 370.1; 356/600, 622, 239.3, 239.7, 239.8, 237.2, 237.4; 348/86–93, 94–95, 125–134

(56) References Cited

U.S. PATENT DOCUMENTS 5,037,202 A * 8/1991 Batchelder et al. .......... 356/336
5,712,701 A * 1/1998 Clementi et al. .......... 356/237.2
5,852,671 A * 12/1998 Oshima ...................... 382/154

OTHER PUBLICATIONS

Stanley Wolf and Richard N. Tauber; *Silicon Processing for the VLSI Era, Vol. 1: Process Technology*; pp. 446–452 and 483–486; 1986.

* cited by examiner

Primary Examiner—Leo Boudreau
Assistant Examiner—Shefali Patel
(74) Attorney, Agent, or Firm—Timothy M. Honeycutt

(57) ABSTRACT

Methods and apparatus for inspecting a feature on a wafer surface are provided. In one aspect a method of inspecting a feature on a film surface is provided that includes illuminating the feature with laser radiation and detecting radiation scattered from the feature with a plurality of detectors. Each of the plurality of detectors has a known position. A position of the feature observed by each of the plurality detectors is computed based upon the radiation scattered from the feature. An average position of the positions observed by each of the plurality of detectors is computed. A first value for each of the plurality of detectors is computed that is the scalar product of the known position of a given detector with the difference of the position of the feature observed by that given detector and the average of the positions observed by each of the plurality of detectors. A second value or scatter height descriptor indicative of the topography of the feature is computed by summing first values for the plurality of detectors.

19 Claims, 3 Drawing Sheets

METHOD AND APPARATUS FOR INSPECTING WAFER DEFECTS

BACKGROUND OF THE INVENTION

1. Field of the Invention

This invention relates generally to semiconductor fabrication, and more particularly to methods and apparatus for inspecting features on a wafer surface.

2. Description of the Related Art

Wafer inspections are routinely performed at numerous stages during the processing of semiconductor integrated circuits. Two common inspection points include after-develop-inspection ("ADI") and post-chemical-mechanical-polishing ("CMP") inspection. ADI is performed to ensure that the steps leading up to and including resist develop have been performed correctly and to within the specified tolerances for the particular process. The goals of the ADI procedure are to verify that the correct mask has been used, that the resist film is free from contamination, scratches, bubbles, striations, etc., and that the defect types and populations are cataloged to enable subsequent yields and defect occurrences to be correlated.

The goals of post CMP inspection procedure are to ensure that the polished film exhibits an acceptable level of defects in the form of surface particles, pits or craters and scratches. It is desirable for the post CMP inspection procedure to not only identify the locations of defects on the polished film but also to characterize the topography of the defects, that is, whether the defects are pits or surface particles. The need to distinguish pits and craters from surface particles arises because such classes of defects are the product of quite different mechanisms during CMP processing, and thus entail different remedial measures. Surface particles on the polished film may indicate the presence of particulate contaminants originating from the CMP tool polish pad, the slurry or from another source. Pits or craters on the other hand are frequently the result of rip-outs that occur during CMP. Rip-outs are usually caused by poor process control during CMP. Typical causes for such poor CMP process control include, for example, undesirably large abrasive particles in the CMP slurry, undesirable variations in pad pressure applied to the polished surface, and irregular dispersion of CMP slurry during CMP to name just a few. Some types of films are more susceptible to rip-out than others. For example, tetra-ethyl-ortho-silicate ("TEOS") films often exhibit higher rates of CMP rip-out than other types of insulator materials. This propensity for CMP rip-out for TEOS is due largely to the kinetics of the chemical vapor deposition processes used to form such films.

Conventional techniques for detecting defects in resist and CMP films include, for example, optical microscopy and laser scanning. In optical microscopy inspection, a human operator visually inspects the surface of the resist or polished film to identify and catalog defects. Given the immense quantities of defects typically present on a resist or polished film, the operator only observes a small quantity of defects in selected areas of the film. Furthermore, the operator will typically inspect only a small percentage of the wafers in a given lot. During the inspection, the operator catalogs the defects observed and characterizes them based on topography, that is, as a pit or crater or a surface particle. From the very limited sampling, predictions are then made about the size and composition of the defect population for not only the wafer inspected but also for the overall lot of wafers. Although the human operator is in many cases able to distinguish surface particles from pits in the inspected film, the process is time consuming and may yield inaccurate predictions about the size and composition of the defect population for a given wafer or lot of wafers since inspection time constraints only allow for a relatively small percentage of a film surface to be visually inspected.

Laser scanning defect inspection has eliminated some of the time constraints that are associated with human operator optical inspection. In many conventional laser inspection systems, a laser is focused down to a relatively small spot which is then scanned across the surface of the resist or polished film. Light reflected off the film is detected by two or more photodetectors that are positioned on either side of the scan axis. The detectors are designed to read the intensity of the scattered radiation. In many cases, current laser defect inspection systems do an acceptable job of identifying and distinguishing flat plane defects, such as pattern defects. However, current laser scanning systems do a relatively poor job of identifying the topography of a particular defect, that is, whether the defect is a pit or a surface particle. The difficulty stems from the fact that the average intensity of scattered radiation from a given size pit or surface particle is about the same. Thus, while conventional laser scanning techniques may be used to more quickly identify the total population of defects on a given film, the exact composition of the population of defects may not be determined.

The present invention is directed to overcoming or reducing the effects of one or more of the foregoing disadvantages.

SUMMARY OF THE INVENTION

In accordance with one aspect of the present invention, a method of inspecting a feature on a film surface is provided that includes illuminating the feature with laser radiation and detecting radiation scattered from the feature with a plurality of detectors. Each of the plurality of detectors has a known position. A position of the feature observed by each of the plurality detectors is computed based upon the radiation scattered from the feature. An A first value for each of the plurality of detectors is computed that is the scalar product of the known position of a given detector with the difference of the position of the feature observed by that given detector and the average of the positions observed by each of the plurality of detectors. A second value indicative of the topography of the feature is computed by summing first values for the plurality of detectors.

In accordance with another aspect of the present invention, a method of inspecting a feature on a film surface is provided that includes illuminating the feature with laser radiation and detecting radiation scattered from the feature with D detectors. Each of the D detectors has a known position $\vec{u}_d$ where d designates a given detector. A position $\vec{p}_d$ of the feature observed by each of the D detectors is computed based upon the radiation scattered from the feature. An average position $\vec{P}$ of the positions $\vec{p}_d$ observed by each of the D detectors is computed and a scatter height descriptor S for the feature is computed according to the equation:

$$S = \frac{\sum_d (\vec{p}_d - \vec{P}) \cdot \vec{u}_d}{D}.$$

In accordance with another aspect of the present invention, a method of inspecting a film surface is provided that includes subdividing the film surface into a plurality of pixel locations and sequentially illuminating each of the pixel locations with laser radiation. Radiation scattered from each of the pixel locations is detected with D detectors, where each of the D detectors has a known position $\vec{u}_d$ where d designates a given detector. A position $\vec{p}_d$ of each of a plurality of defects on the film surface observed by each of the D detectors is computed according to the equation:

$$\vec{p}_d = \frac{\sum_{ij} \vec{p}_{ij} I_{ijd}}{\sum_{ij} I_{ijd}},$$

where $I_{ijd}$ is the intensity of scattered laser radiation detected by a given detector d for a given pixel location $\vec{P}_{ij}$. An average position $\vec{P}$ of the positions $\vec{p}_d$ observed by each of the D detectors is computed according to by the equation:

$$\vec{P} = \frac{\sum_{ijd} \vec{p}_{ij} I_{ijd}}{\sum_{ijd} I_{ijd}}.$$

A scatter height descriptor S for each of the plurality of defects is computed according to the equation:

$$S = \frac{\sum_d (\vec{p}_d - \vec{P}) \cdot \vec{u}_d}{D}.$$

In accordance with another aspect of the present invention, an inspection apparatus is provided that includes means for holding a workpiece, means for illuminating a feature on the workpiece with laser radiation, and a plurality of detectors that are operable to detect laser radiation scattered from the feature. Each of the detectors has a known location. The apparatus also includes means for determining a position of the feature observed by each of the plurality detectors based upon the radiation scattered from the feature, computing an average position of the positions observed by each of the plurality of detectors, computing a first value for each of the plurality of detectors, where the first value is the scalar product of the known position of a given detector with the difference of the position of the feature observed by that given detector and the average of the positions observed by each of the plurality of detectors, and computing a second value indicative of the topography of the feature by summing first values for the plurality of detectors.

BRIEF DESCRIPTION OF THE DRAWINGS

The foregoing and other advantages of the invention will become apparent upon reading the following detailed description and upon reference to the drawings in which.

DETAILED DESCRIPTION OF SPECIFIC EMBODIMENTS

Figure 1:
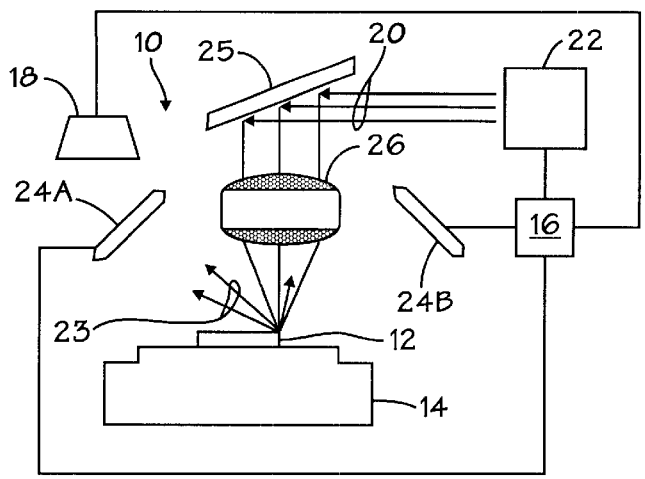
FIG. 1 is a side schematic view of an exemplary embodiment of a laser inspection tool with which a method in accordance with the present invention may be practiced.

In the drawings described below, reference numerals are generally repeated where identical elements appear in more than one figure. Turning now to the drawings, and in particular to FIG. 1, therein is shown a side schematic view of an exemplary embodiment of a semiconductor wafer or workpiece laser inspection tool 10 ("tool 10"). The tool 10 is operable to scan features on the surface of a semiconductor wafer or workpiece 12. A stage 14 is provided for holding the workpiece 12. The stage 14 is operable to rotate in a horizontal plane to align the workpiece 12 prior to scanning. The movements of the stage 14 are regulated by an electronic controller 16, which may be a programmable controller, a computer or the like. An optical scanner 18 capable of pattern recognition is provided for optically scanning the surface of the workpiece 12 to search for alignment marks or other surface features on the workpiece 12 which enable the controller 16 to manipulate the stage 14 and accurately align the workpiece 12.

Scanning of the workpiece 12 is accomplished by striking the surface of the workpiece 12 with an incident beam 20 from a laser 22 and detecting the intensity of scattered radiation 23 with one or more detectors 24A and 24B. The tool 10 is provided with two additional detectors 24C and 24D which are not visible in FIG. 1, but which are shown in subsequent figures. The incident beam 20 of laser radiation is initially reflected off a reflecting mirror 25, then passed through a focusing lens 26 that is movable in a horizontal plane to enable the surface of the workpiece 12 to be scanned in a preselected pattern. The controller 16 is operable to control not only the operation of the stage 14 and the optical scanner 18, but also the operation of the laser 22 and the detectors 24A and 24B.

Figure 2:
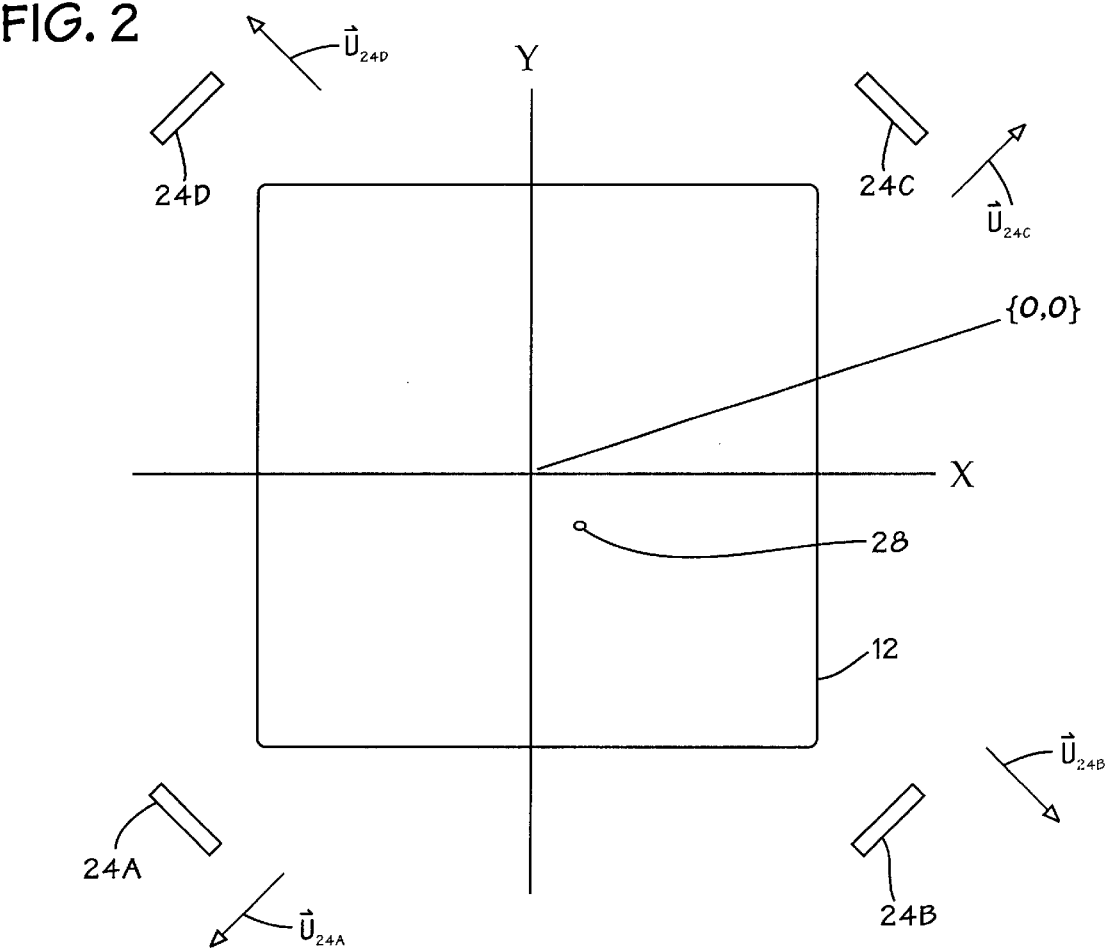
FIG. 2 is an overhead view of a workpiece positioned in the inspection tool of FIG. 1 in accordance with the present invention.
Figure 3:
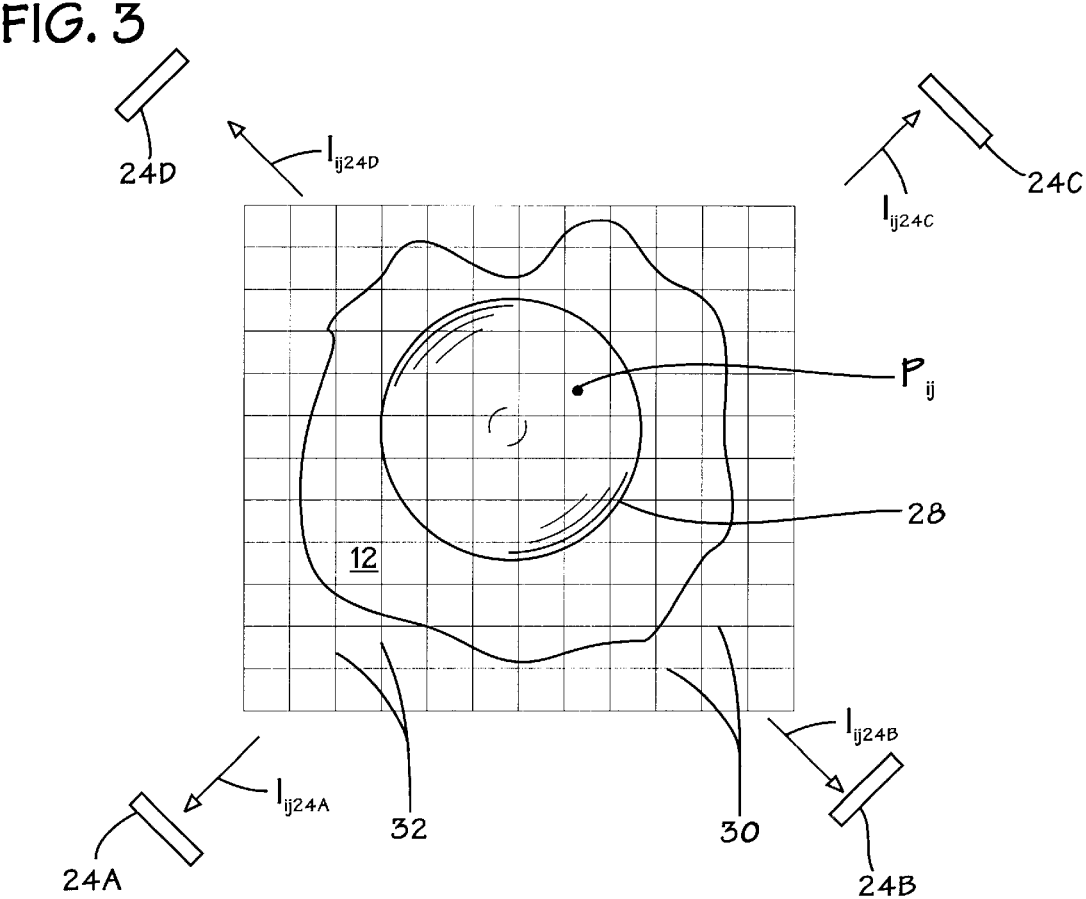
FIG. 3 is a highly magnified overhead view of an exemplary defect on the workpiece depicted in FIG. 2.

An exemplary method of inspecting a feature on the workpiece 12 may be understood by referring now to FIGS. 2 and 3. FIG. 2 is an overhead view of the workpiece 12 and detectors 24A, 24B, 24C and 24D. To better illustrate the method, a hypothetical defect 28 is shown on the workpiece 12. FIG. 3 is a highly magnified overhead view of the portion of the workpiece 12 on which the defect 28 is located. After the controller 16 in conjunction with the optical scanner 18 and the stage 14 accurately align the workpiece 12, the controller 16 electronically computes an overlaying grid pattern based upon an x-axis and an y-axis having an origin {0,0}. As shown in FIG. 3, the grid consists of a plurality of intersecting horizontal and vertical lines 30 and 32 respectively, which define a plurality of pixels, one of which is designated $P_{ij}$. In an exemplary embodiment, the laser inspection of the workpiece 12 is 2f) carried out by laser scanning via a raster scan of the various pixels. However, other well known scanning patterns may be used.

The positions of the detectors 24A, 24B, 24C and 24D relative to the origin {0,0} are respectively given by unit vectors $\vec{u}_{24A}$, $\vec{u}_{24B}$, $\vec{u}_{24C}$ and $\vec{u}_{24D}$. As the workpiece 12 is laser scanned at each pixel location, the detectors 24A, 24B, 24C and 24D sense the intensity of the laser light scattered from the workpiece 12. For the exemplary pixel $P_{ij}$, the detector 24A senses the intensity of laser radiation scattered at the pixel point $P_{ij}$ as represented by the quantity $I_{ij24A}$. In like fashion, detectors 24B, 24C and 24D respectively sense the scattered radiation as represented by the quantities $I_{ij24B}$, $I_{ij24C}$ and $I_{ij24D}$. The controller 16 receives the quantities $I_{ij24A}$, $I_{ij24B}$, $I_{ij24C}$ and $I_{ij24D}$ and from them determines if the pixel $P_{ij}$ corresponds to a defect location or a non-defect location. Virtually all inspection tools must differentiate pixel locations corresponding to defects from pixel locations corresponding to normal structures. This may be accomplished by the tool 10 in a variety of ways in accordance with the present invention. For example, the quantities $I_{ij24A}$, $I_{ij24B}$, $I_{ij24C}$ and $I_{ij24D}$ may be compared to a fixed intensity threshold. If the intensity quantities $I_{ij24A}$, $I_{ij24B}$, $I_{ij24C}$ and $I_{ij24D}$ associated with the pixel $P_{ij}$ are above the threshold, the pixel $P_{ij}$ is determined to be part of a defect. Alternatively, a more complex comparison may be made to improve the sensitivity of the inspection tool 10. For example, the intensity quantities for a given pixel, in this case the quantities $I_{ij24A}$, $I_{ij24B}$, $I_{ij24C}$ and $I_{ij24D}$ for the pixel $P_{ij}$, may be compared to those of a corresponding pixel in a neighboring die or on a neighboring wafer. In another option, multiple intensity thresholds which depend on the surrounding environment of the pixels in both the reference and inspected die or wafer may be used.

When the intensity is read by the detectors 24A, 24B, 24C and 24D at those pixel locations coinciding with the defect 28, the intensity readings will accordingly correspond to light scattered from the defect 28. The intensity readings for the plurality of pixels associated with the defect 28 are aggregated or clustered by the controller 16 to produce a digital image of the defect 28 with a particular location as observed by each of the detectors 24A, 24B, 24C and 24D.

Figure 4:
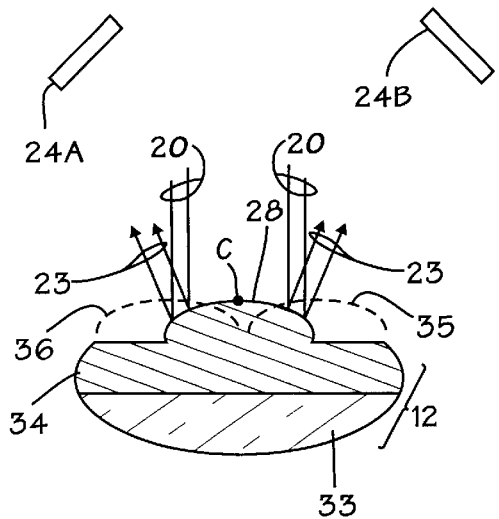
FIG. 4 is a cross-sectional view of the defect depicted in FIG. 3 showing light scattering off the defect and sensed by one or more detectors.

The observed location of the defect 28 may shift between the various detectors 24A, 24B, 24C and 24D depending upon their locations relative to the origin {0,0} and on the topography of the defect 28, e.g., pit or hole versus a surface particle. The phenomena is illustrated for an exemplary surface particle defect 28 in FIG. 4, which is a cross-sectional view of the workpiece 12 taken through the defect 28. For this illustration, the workpiece consists of a substrate 33 and an overlying film 34. The film 34 may be a resist film, a metallization layer, an insulating film or virtually any other type of film used in semiconductor fabrication. Optionally, the inspection may be carried out on the bare substrate 33. The approximate center of the defect 28 is labeled point C. Incident light rays 20 striking the defect 28 to the right of the center point C will produce scattered rays 23 which are detected by detector 24B. However, those incident rays 20 striking the defect 28 to the left of the center point C will generally scatter away from detector 24B and produce scattered rays 23 that travel toward the detector 24A. As a consequence, detector 24B observes, in essence, only a portion of the defect 28. This results in the controller 16 interpreting the intensity data from detector 24B as corresponding to the position of the defect 28 being shifted to the right as shown by the dashed FIG. 35. The similar, albeit opposite effect results for scattered radiation observed by detector 24A. In this case, the observed location of the defect 28 will be shifted toward the detector 24A as indicated by the dashed FIG. 36.

Figure 5:
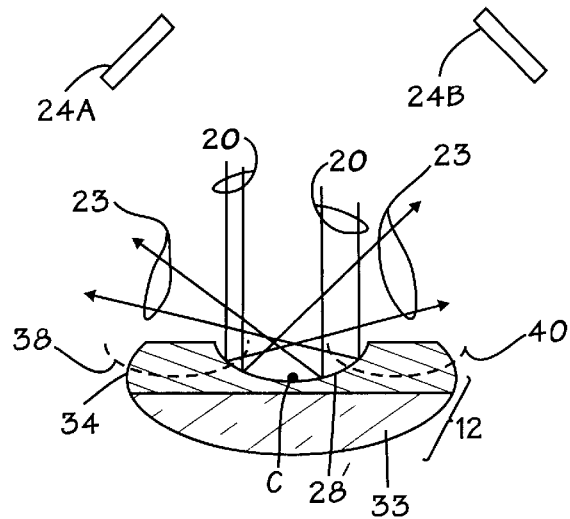
FIG. 5 is a cross-sectional view similar to FIG. 4 but depicting a crater-like defect and its associated light scattering.

The opposite effect will occur if the defect 28 is a pit instead of a particle. FIG. 5 is a cross-sectional view similar to FIG. 4, but depicts the defect, now designated 28', as a pit instead of a particle. The center of the defect 28' is again designated C. In this illustration, incident light rays 20 striking to the left of the center point C strike the pit 28' and produce scattered rays 23 which travel toward detector 2413. However, those incident rays 20 striking to right of point C will produce scattered rays 23 which travel toward detector 24A. As a result, detector 24B willbe effectively blind to the portion of the defect 28' falling to the right of the center point C. The controller 16 will thus interpret the intensity data sensed by detector 24B as corresponding to a position of the defect 28' that is shifted to the left of the actual position of the defect 28' and thus away from detector 24B as illustrated by the dashed FIG. 38. In like fashion, the observed location of the defect 28' will be shifted to the right and thus away from the actual location of the defect 28' as illustrated by the dashed figure 40.

Figure 6:
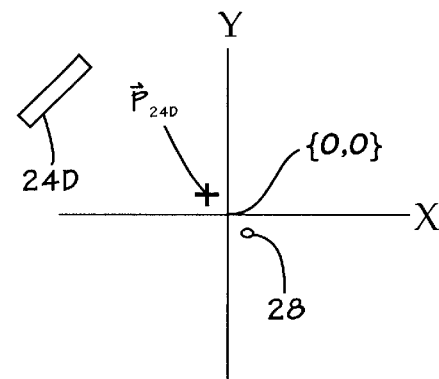
FIG. 6 is a graphical representation of the observed versus actual positions of a defect as seen by four detectors in the inspection tool of FIG. 1.
Figure 6:
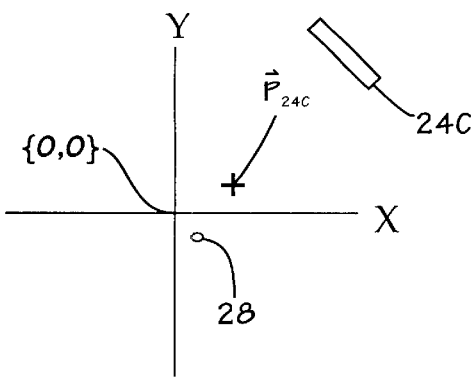
Figure 6:
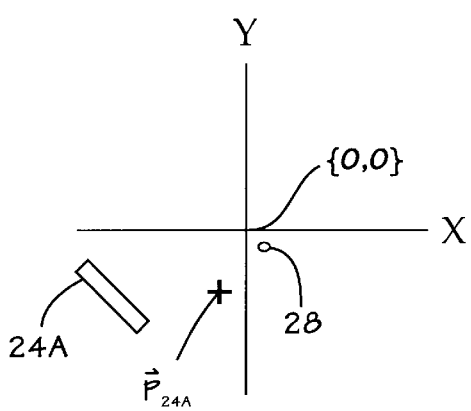
Figure 6:
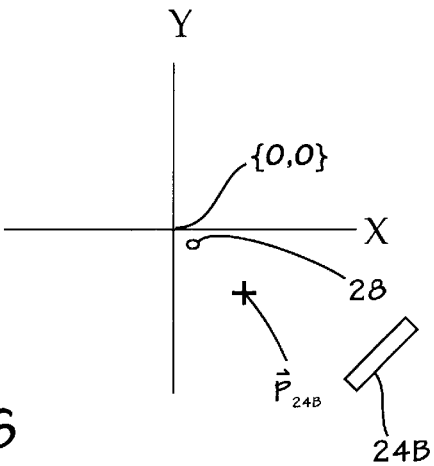

The shifts between the actual and observed locations of the defect 28 for each of the detectors 24A, 24B, 24C and 24D may be understood by referring now to FIG. 6, which is a plan view of the x-y axis of FIG. 2 replicated separately for each of the detectors 24A, 24B, 24C and 24D. Each of the x-y plots shows the actual location of the defect 28 and the observed location of the defect for a given detector, e.g., 24A, 24B, 24C or 24D. For example, the point $\vec{p}_{24A}$ represents the observed location of the defect 28 as observed by detector 24A. Points $\vec{p}_{24B}$, $\vec{p}_{24C}$ and $\vec{p}_{24D}$ represent, respectively, the observed locations of the defect 28 observed by the detectors 24B, 24C and 24D. Note that in each case, the observed position of the defect, e.g., $\vec{p}_{24A}$, $\vec{p}_{24B}$, etc., is shifted toward the position of the given detector 24A, 24B, etc. This is a result of the aforementioned phenomena associated with light scattering from a surface particle defect, such as that depicted in FIG. 4. Note that points $\vec{p}_{24A}$, $\vec{p}_{24D}$ are vector quantities with respective directions measured relative to the origin {0,0}.

The shifts between the actual and observed positions for the defect 28 may be used to define a scatter height descriptor, S, which serves as an index to indicate whether or not the defect 28 is a pit or a surface particle. The scatter height descriptor, S, is given by the following formula:

$$S = \frac{\sum_d (\vec{p}_d - \vec{P}) \cdot \vec{u}_d}{D} \quad \text{Equation 1}$$

where d is the number of a given detector, e.g., 24A, 24B, 24C or 24D, the quantity $\vec{p}_d$ is the position of the defect 28 seen by a given detector d, e.g., $\vec{p}_{24A}$, $\vec{p}_{24D}$, the quantity $\vec{p}$ is the average position of the positions of the defect 28 as seen by all of the detectors 24A, 24B, 24C and 24D, $\vec{u}_d$ is the unit vector for a given detector, e.g, 24A, 24B, 24C or 24D, and the quantity D is the total number of detectors 24A, 24B, 24C and 24D. Note that is desirable for the magnitude of the scatter height descriptor, S, to be independent of the number of detectors. Accordingly, the summed quantity in Equation 1 is divided by the total number of detectors D so that the scatter height descriptor, S, is normalized.

The quantity $\vec{p}_d$ in Equation 1 is given by the following equation:

$$\vec{p}_d = \frac{\sum_{ij} \vec{p}_{ij} I_{ijd}}{\sum_{ij} I_{ijd}} \quad \text{Equation 2}$$

where $\vec{p}_{ij}$ is the position of a given pixel in the pixel pattern depicted in FIG. 3, and $I_{ijd}$ is the intensity of scattered radiation detected by a given detector 24A, 24B, 24C or 24D at a given pixel location.

The average position $\vec{p}$ set forth in Equation 1 above is given by the following equation:

$$\vec{P} = \frac{\sum_{ijd} \vec{p}_{ij} I_{ijd}}{\sum_{ijd} I_{ijd}} \quad \text{Equation 3}$$

Figure 7:
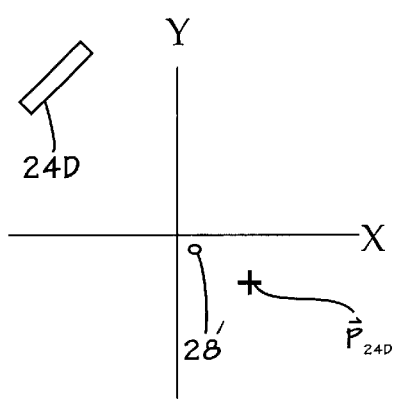
FIG. 7 is a graphical representation like FIG. 6 depicting the actual versus observed positions of the defect where the defect is a depression or hole instead of a surface particle.
Figure 7:
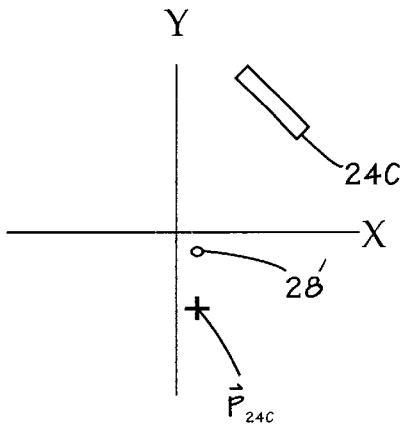
Figure 7:
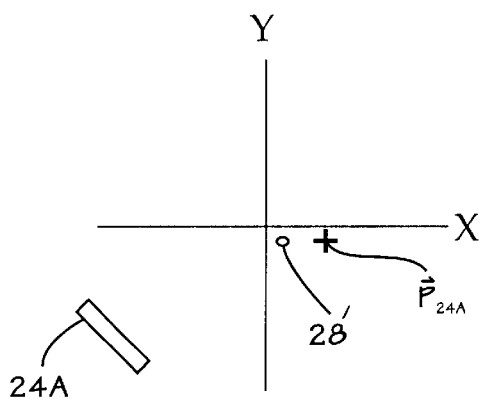
Figure 7:
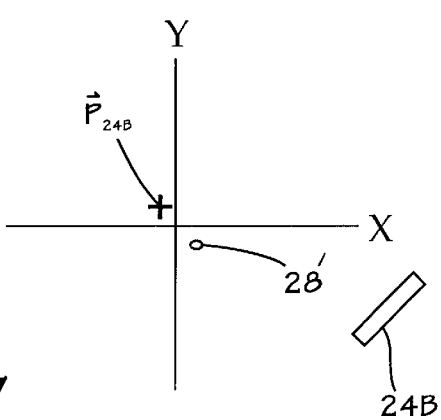

The scatter height descriptor, S, is a scalar quantity that provides a straightforward indicator of the character of the defect 28. A positive value for S is the result of the observed location of the defect 28 being shifted toward the various detectors 24A, 24B, 24C and 24D and thus is an indication that the defect 28 is a particle. Conversely, a negative value for S results if the observed location of the defect 28 is shifted away from the various detectors 24A, 24B, 24C and 24D and thus is an indication that the defect 28 is a pit or crater. An example of the shift between the actual and observed locations for the pit defect 28' resulting in a negative value for S is shown in FIG. 7, which is a plan view of multiple plots like FIG. 6.

While the sign of the scatter height descriptor, S, is indicative of the topography of the defect 28 or 28', the magnitude of S is an indicator of the reliability of the characterization of the defect 28 or 28' as a pit or a particle in view of the sign of S. Relatively larger magnitudes for S provide a greater assurance that the sign of S is a true indicator of the topography of the defect 28 or 28'.

The use of the scatter height descriptor, S, is independent of the number of detectors 24A, 24B, 24C and 24D and is largely independent of their locations so long as those locations are known. It is anticipated that the accuracy of the topography characterization for the defect 28 or 28' using the scatter height descriptor, S, will increase where the detectors 24A, 24B, 24C and 24D are positioned at relatively low angles with respect to the upper surface of the workpiece 12. This is due to the fact that the shift between the observed and actual positions of the defect 28 or 28' will be much less pronounced if the detectors 24A, 24B, 24C and 24D are located directly above the defect 28 or 28'. In addition, the use of the scatter height descriptor, S, is independent of the wavelength of coherent radiation and the type of tool used for inspection. In an exemplary embodiment, an Applied Materials Model WF-736 is employed.

A variety of output signals may be generated by the tool 10 during the inspection of the workpiece 12. For example, an output signal based on the scatter height descriptor, S, may be generated and used to characterize defects on the workpiece 12. In addition, a signal providing a defect count may be generated. If desired, the scatter height descriptor, S, may be used in conjunction with other commonly used descriptors to provide a more complete picture of not only the size but also the composition of the defect population on a given workpiece. The output signals may be generated by the controller 16 or other device as desired and may be in human readable format or code for use with another computing device (not shown). It is anticipated that the laser inspection with scatter height descriptor S computation may be readily used for automatic defect classification (ADC).

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents and alternatives falling within the spirit and scope of the invention as defined by the following appended claims.

What is claimed is:

1. A method of inspecting a feature on a film surface, comprising:

illuminating the feature with laser radiation;

detecting radiation scattered from the feature with a plurality of detectors, each of the plurality of detectors having a known position;

computing a position of the feature observed by each of the plurality detectors based upon the radiation scattered from the feature;

computing an average position of the positions observed by each of the plurality of detectors;

computing a first value for each of the plurality of detectors, the first value being the scalar product of the known position of a given detector with the difference of the position of the feature observed by that given detector and the average of the positions observed by each of the plurality of detectors; and computing a second value indicative of the topography of the feature by summing first values for the plurality of detectors.

2. The method of claim 1, comprising forming an output signal based on the second value.

3. The method of claim 2, wherein the computing of the positions of the feature observed by each of the plurality of detectors, the average position of the positions observed by each of the detectors, and the second value and the formation of the output signal is performed with an electronic controller.

4. The method of claim 3, wherein the electronic controller comprises a computer.

5. The method of claim 1, wherein the feature is scanned in a pixel pattern having a plurality of pixel locations.

6. The method of claim 1, wherein the intensity of the scattered radiation is detected by the plurality of detectors.

7. A method of inspecting a feature on a film surface, comprising:

illuminating the feature with laser radiation;

detecting radiation scattered from the feature with D detectors, each of the D detectors having a known position $\vec{u}_d$ and d designating a given detector; computing a position $\vec{p}_d$ of the feature observed by each of the D detectors based upon the radiation scattered from the feature;

computing an average position $\vec{p}$ the positions $\vec{u}_d$ observed by each of the D detectors; and computing a scatter height descriptor S for the feature determined by the equation:

$$S = \frac{\sum_d (\vec{p}_d - \vec{P}) \cdot \vec{u}_d}{D}.$$

8. The method of claim 7, wherein the feature is scanned in a pixel pattern having a plurality of pixel locations $\vec{p}_{ij}$, the position $\vec{u}_d$ of the feature observed by each of the detectors is determined by the equation:

$$\vec{p}_d = \frac{\sum_{ij} \vec{p}_{ij} I_{ijd}}{\sum_{ij} I_{ijd}},$$

the average position $\vec{P}$ of the positions $\vec{u}_d$ is determined by the equation:

$$\vec{P} = \frac{\sum_{ijd} \vec{p}_{ij} I_{ijd}}{\sum_{ijd} I_{ijd}},$$

whereby $I_{ijd}$ is the intensity of scattered laser radiation detected by a given detector d for a given pixel location $\vec{p}_{ij}$.

9. The method of claim 8, wherein the computing of the position $\vec{p}_d$ of the feature observed by each of the D detectors based upon the radiation scattered from the feature, the average position $\vec{p}$ of the positions $\vec{p}_d$ observed by each of the D detectors, and the scatter height descriptor S is performed with an electronic controller.

10. The method of claim 9, wherein the electronic controller comprises a computer.

11. The method of claim 9, wherein the electronic controller characterizes the feature as an opening in the film if S is negative, or as a particle on the film if S is positive.

12. A method of inspecting a film surface, comprising:

subdividing the film surface into a plurality of pixel locations;

sequentially illuminating each of the pixel locations with laser radiation;

detecting radiation scattered from each of pixel locations with D detectors, each of the D detectors having a known position $\vec{u}_d$, d designating a given detector;

computing a position $\vec{p}_d$ of each of a plurality of defects on the film surface observed by each of the D detectors determined by the equation:

$$\vec{p}_d = \frac{\sum_{ij} \vec{p}_{ij} I_{ijd}}{\sum_{ij} I_{ijd}},$$

whereby $I_{ijd}$ is the intensity of scattered laser radiation detected by a given detector d for a given pixel location $\vec{p}_{ij}$;

computing an average position $\vec{P}$ of the positions $\vec{u}_d$ observed by each of the D detectors determined by the equation:

$$\vec{P} = \frac{\sum_{ijd} \vec{p}_{ij} I_{ijd}}{\sum_{ijd} I_{ijd}};$$

and computing a scatter height descriptor S for each of the plurality of defects determined by the equation:

$$S = \frac{\sum_d (\vec{p}_d - \vec{P}) \cdot \vec{u}_d}{D}.$$

13. The method of claim 12, wherein the computing of the position $\vec{p}_d$ of each of the plurality of defects, the average position $\vec{P}$ of the positions $\vec{p}_d$, and the scatter height descriptor S is performed with an electronic controller.

14. The method of claim 13, wherein the electronic controller comprises a computer.

15. The method of claim 13, wherein the electronic controller characterizes the feature as an opening in the film if S is negative, or as a particle on the film if S is positive.

16. An inspection apparatus, comprising:

means for holding a workpiece;

means for illuminating a feature on the workpiece with laser radiation;

a plurality of detectors being operable to detect laser radiation scattered from the feature, each of the detectors having a known location; and means for determining a position of the feature observed by each of the plurality detectors based upon the radiation scattered from the feature, computing an average position of the positions observed by each of the plurality of detectors, computing a first value for each of the plurality of detectors, the first value being the scalar product of the known position of a given detector with the difference of the position of the feature observed by that given detector and the average of the positions observed by each of the plurality of detectors, and computing a second value indicative of the topography of the feature by summing first values for the plurality of detectors.

17. The inspection apparatus of claim 16, wherein the means for determining comprises an electronic controller.

18. The inspection apparatus of claim 17, wherein the electronic controller comprises a computer.

19. The method of claim 16, wherein means for illuminating is operable to scan the feature in a pixel pattern having a plurality of pixel locations.

* * * * *

UNITED STATES PATENT AND TRADEMARK OFFICE
CERTIFICATE OF CORRECTION

PATENT NO. : 6,574,359 B1
DATED : June 3, 2003
INVENTOR(S) : Bryon K. Hance

It is certified that error appears in the above-identified patent and that said Letters Patent is hereby corrected as shown below:

Column 8,
Line 48, insert -- of -- before "the";

Line 60, delete " $\vec{u}\,d$ " and substitute -- $\vec{p}\,d$ -- therefor;

Column 9,
Lines 1 and 49, delete " $\vec{u}\,d$ " and substitute -- $\vec{p}\,d$ -- therefor;

Line 32, insert -- the -- before "pixel";

Column 10,
Line 33, insert -- of -- after "plurality"; and
Line 48, insert -- the -- before "means".

Signed and Sealed this

Eighth Day of February, 2005

JON W. DUDAS
*Director of the United States Patent and Trademark Office*